United States Patent [19]

Utterberg

[11] Patent Number: 5,047,021
[45] Date of Patent: Sep. 10, 1991

[54] MALE LUER LOCK MEDICAL FITTING

[76] Inventor: David S. Utterberg, 1080 Chestnut St., Apt. 4A, San Francisco, Calif. 94109

[21] Appl. No.: 627,889

[22] Filed: Dec. 13, 1990

Related U.S. Application Data

[63] Continuation of Ser. No. 400,827, Aug. 29, 1989, abandoned.

[51] Int. Cl.⁵ .............................................. A61M 25/00
[52] U.S. Cl. .................................. 604/283; 604/256; 604/905; 285/332
[58] Field of Search ................... 604/28, 29, 256, 280, 604/283, 411, 905; 285/332

[56] References Cited

U.S. PATENT DOCUMENTS

| | | | |
|---|---|---|---|
| 3,616,866 | 11/1971 | Verheul et al. | 285/232 X |
| 3,751,077 | 8/1973 | Hiszpanski | 285/232 X |
| 4,187,846 | 2/1980 | Lolachi et al. | 604/411 |
| 4,266,815 | 5/1981 | Cross | 604/283 X |
| 4,296,949 | 10/1981 | Muetterties et al. | 604/905 X |
| 4,439,188 | 3/1984 | Dennehey et al. | 604/283 |
| 4,452,473 | 6/1984 | Rusclke | 604/283 X |
| 4,504,268 | 3/1985 | Herlitze | 604/170 |
| 4,607,868 | 8/1986 | Harvey et al. | 285/332 |
| 4,629,455 | 12/1986 | Kanno | 604/241 |
| 4,639,019 | 1/1987 | Mittleman | 285/332 |
| 4,963,132 | 10/1990 | Gibson | 604/256 |
| 4,969,879 | 11/1990 | Lichte | 604/283 |

OTHER PUBLICATIONS

International Standard ISO 594/1-1986(E) pages 1 through 7.
American National Standard-ANSI/HIMA MD70.1-1983-18 pages.

Primary Examiner—C. Fred Rosenbaum
Assistant Examiner—Adam J. Cermak
Attorney, Agent, or Firm—Garrettson Ellis

[57] ABSTRACT

A male luer lock fitting, having an elongated nozzle and an internally threaded locking ring mounted around the nozzle. The locking ring has complete freedom to rotate about the nozzle axis, and limited freedom to translate along the nozzle axis. The length of the nozzle which extends outward from locking ring is chosen so that the inventive device is capable of piercing commonly used medical fluid container ports. The nozzle and locking ring are designed to have relative dimensions which enable a user to disconnect the inventive device easily from a female luer lock. Preferably, the inventive device is dimensioned to meet the ANSI/HIMA MD70.1 and ISO standards.

10 Claims, 3 Drawing Sheets

MALE LUER LOCK MEDICAL FITTING

This application is a continatuion of application 07/400,824 filed Aug. 29, 1989, now abandoned.

FIELD OF THE INVENTION

The invention is a male luer lock fitting, having a threaded ring and a nozzle designed to pierce commonly used IV fluid container access ports as well as perform its primary function of mating with a female luer lock fitting.

BACKGROUND OF THE INVENTION

Male and female luer taper fittings are conventionally employed to connect disposable medical devices (such as a syringe and a needle) in a liquid and air leakproof manner. After they have been connected (pushed together), luer taper fittings remain together solely due to friction between their mating tapered surfaces. They may readily be disconnected by twisting and pulling the female and male fittings away from each other.

Various additional design components have been employed with luer taper fittings to increase their connection strength. Increased connection strength is needed, for example, to accommodate high pressure fluid flow through the connected fittings or for extra protection against the loss of high risk fluids such as a patient's blood in a hemodialysis procedure. Luer lock fittings are an example of this class of "enhanced" luer taper fittings.

Conventional female luer lock fitting 5 is shown in FIG. 1. Conventional male luer lock fitting 6 is shown in FIG. 2. Tapered nozzle 10 of lock fitting 6 is dimensioned to fit tightly inside tapered socket 11 of lock fitting 5 as fitting 6 is screwed onto fitting 5. When lock fittings 5 and 6 are connected, fluid may flow between central fluid passage 16 of fitting 6 and central fluid passage 17 of fitting 5. Fitting 6 includes locking ring 12 (sometimes referred to as a "collar"), which has an internal threaded portion 14. Fitting 5 has an annular lug 15, which is dimensioned so that lug 15 may be screwed into threaded portion 14 of fitting 6, as nozzle 10 is inserted into socket 11.

Conventionally, luer lock ring 12 may be fixed 0 to nozzle portion 10 as shown in FIG. 2, or it may be a separate component from the nozzle that is free to move rotationally but not longitudinally (a "free/restricted ring"), or free to move rotationally and partially free to move longitudinally (a "free/partially restricted" ring) in which case the distal ring threads are still in contact with the female lugs after the ring has been untwisted until it encounters its restriction, or free to move both rotationally and longitudinally (a "free ring") in which case the ring threads may be completely unscrewed from the female lugs before the ring encounters any longitudinal restriction.

Industry standards have been established (and others proposed) for standardizing the dimensions of luer lock fittings (of the fixed type shown in FIGS. 1 and 2, the free type shown in FIG. 2a, and the free/partially restricted type shown in FIGS. 9 and 10). One such standard is the American National Standard Institute/Health Industry Manufacturers Association MD70.1 standard, adopted in 1983 (hereinafter, the "ANSI/HIMA" or the "ANSI/HIMA MD70.1" standard), and another is the ISO/DIS 594-2 proposed standard (hereinafter, the "ISO" standard).

In FIG. 2, fixed ring 12 is shown to be integrally formed with nozzle 10. Alternatively, ring 12 and nozzle 10 may be separately manufactured, and then attached together to form a rigid assembly. To connect male fitting 6 of FIG. 2 with female fitting 5 of FIG. 1, threads 14 of fitting 6 must be screwed onto lugs 15 of fitting 5.

In the case of a free ring (with both rotational and longitudinal freedom) such as that shown in FIG. 2a, two steps must be performed in order to separate a male free ring fitting from a female fitting (such as fitting 5 shown in FIG. 1) after they have been screwed together. First, the fittings must be unscrewed until lugs 15 of the female fitting are released from threads 24 of free ring 22. Then, nozzle 20 and female socket 11 must be twisted and pulled apart (since the tip of nozzle 20 will still remain in contact with socket 11 immediately after lugs 15 have been released from threads 24) as in the case of conventional luer slip male/female fittings.

The ISO standard requires (among with its other requirements) that the length L of nozzle 20 protruding beyond the end of ring 22 (in its forward position) be not less than 2.10 mm. The ISO standard also specifies that the minimum total length E of nozzle 20 is 7.50 mm, and that the minimum total length F of socket 11 is 7.50 mm.

In FIG. 2a, ring 22 is free to rotate about longitudinal axis Z relative to nozzle 20. Ridge 25 of nozzle 20 restricts upward longitudinal translation of ring 22, to prevent ring 22 from decoupling from nozzle 20, but ring 22 is completely free to translate longitudinally downward relative to nozzle 20. The tip portion of nozzle 20 is conventionally used to puncture (or "spike") IV fluid container access ports, since ring 22 may be retracted out of the way during the puncturing process.

An advantage of a "free ring" male fitting is that it may be mated and locked with a female fitting (and unmated and unlocked from the female fitting) without causing any pronation of the tubes attached to the fittings. This is crucial in preventing kinking or other problems with the tubing. However, a serious disadvantage of conventional free ring male fittings is that they provide no leverage to a user attempting to decouple their nozzle from a female 10 luer fitting after the threads of the free ring have been untwisted from the female luer fitting lugs. Thus, free ring made luer connectors of the type shown in FIG. 2a are difficult to disconnect from female luer fittings.

Yet another conventional male connection fitting (of the "free/partially restricted" type) is shown in FIGS. 9 and 10. Nozzle 400 is shown in its extended position relative to ring 420 in FIG. 9, and in its retracted position in FIG. 10. In FIG. 9, the right end surface 431 of ring 420 abuts shoulder 413 of nozzle 400 so that the top portion of nozzle 400 extends a distance M' leftward from left end surface 433 of ring 420. In FIG. 10, nozzle 400 has been retracted toward the right until shoulder 434 of nozzle 400 abuts ridge 432 of ring 420, so that nozzle 400's tip portion extends a lesser distance L' leftward from left end surface 433. To facilitate decoupling of the FIG. 9-10 fitting from a female luer fitting (not shown), length M' must be sufficiently short that threads 426 of ring 420 are in contact with the lugs at the end of the female fitting in the FIG. 9 configuration (i.e., after ring 420 has been untwisted until end 431 abuts shoulder 413).

This restriction on the length M' allows the last untwisting force applied to ring 420 to be transformed into a "push-off" force for assisting a user to overcome friction between nozzle 400's outer tapered surface 424 and a female luer fitting, in order to decouple nozzle 400 from the female luer fitting. However, this restriction on the length of M' renders tip portion 425 of nozzle too short for spiking commonly used IV fluid container access ports.

In hemodialysis and a number of other medical operations employing luer lock fittings, the luer lock fittings are employed to provide a leak-proof blood flow passage between, for example, a patient access device and an extracorporeal circuit (male nozzle on circuit, female socket on access device). It is also necessary before or after such operations to spike a port in a saline bag with an IV administration set attached to the extracorporeal circuit in order to prime the circuit (before) and rinse the circuit of blood (after). It would be convenient if the male luer lock nozzle could be used to spike the fluid bag port directly, and if the same male luer lock could later be connected to the female luer lock during the same medical operation.

Currently, the only luer lock assembly that can also spike a bag is the "free ring" male luer lock. However, this type of conventional male luer lock is difficult to decouple from a female luer fitting (as explained above).

An example of a commonly used conventional medical fluid container port ("bag port") is shown in FIG. 3. Bag port 200 of FIG. 3 has a cylindrical end portion 201 and a larger diameter body portion 202, which define a shoulder 204 between portions 201 and 202. Membrane 203 separates portions 201 and 202 in order to retain fluid 205 within portion 202. Bag port 200 may be opened by translating a puncturing member toward the left along port axis 206 to pierce (or "spike") membrane 203 (as shown in FIG. 3, which will be discussed below). In one commonly used embodiment of bag port 200, distance D between membrane 203 and the right end of end portion 201, is substantially equal to 9.0 mm, and inner diameter C' of portion 201 is substantially equal to 5.1 mm.

In current practice, there are a number of nonluer lock, male nozzle connectors which are 10 dimensioned properly within the standards to puncture membrane 203 and be frictionally retained by the inner lumen of end portion 201 until removed by the health care worker.

However, conventional male luer locks (whether or not they satisfy the ANSI/HIMA standard) having fixed locking rings (such as the FIG. 2 device), or conventional rings of the "free/restricted" and "free/partially restricted" types, are not capable of spiking the commonly used conventional fluid bag ports. This is because the nozzle of this type of such conventional male luer lock has insufficient length beyond the end of the locking ring (i.e., length L beyond locking ring 12 in FIG. 2) to pierce the bag port membrane (i.e., membrane 203 in FIG. 3), when the end of the locking ring has translated into engagement with the shoulder (shoulder 204 in FIG. 3) between the end and body portions of the bag port.

Some conventional "free ring" male luer lock fittings have been designed with lock rings having sufficient longitudinal freedom of movement, and with male fittings sufficiently long and with a sufficiently narrow transition length, to spike commonly used conventional fluid bag ports (such as that shown in FIG. 3) and be frictionally retained in such ports during the priming and/or rinse back procedure. However these conventional "bag spiking, free ring" male luer locks have the following disadvantages. First, their longitudinal transition portions are so long and narrow that, when connected to female luer locks, the connectors undesirably increase the resistance to fluid flow through the luer connection (and hence the fluid pressure drop through the luer connection). Second, conventional "bag spiking, free ring" male luer locks provide 10 users no mechanical leverage when they attempt to disconnect such male luer locks from female luer locks (as discussed previously). Hemodialysis users, for example, have experienced difficulty in pulling apart such a free ring male lock's nozzle from a female lock's socket (after the female lock has been unscrewed from the threads of the male lock's free ring) because of the increase mating friction due to swelling of the parts into each other during the hemodialysis procedure (typically having two-to-six hour duration, and occurring at 37 degrees Celsius).

It would be desirable to design a bag spiking male luer fitting capable of giving the same significant mechanical advantage in pushing off (decoupling) a female fitting from a male nozzle as it has in connecting with a female fitting. However, it has not been known until the present invention how to combine the bag spiking advantages of conventional free ring male luer locks with the low fluid flow resistance and unlocking leverage of conventional "free/partially restricted" male luer locks. Nor has it been known until the present invention how to design a male luer lock to avoid the described limitations and disadvantages of conventional "bag spiking, free ring" male luer locks, while still being capable of piercing commonly used fluid bag ports.

SUMMARY OF THE INVENTION

The inventive male luer lock connector has a luer taper nozzle with a pair of longitudinally separated nozzle shoulders (or "ridges"), a semielongated longitudinal transition portion (or "length") between the nozzle tip and the ridge nearest the nozzle tip, and an internally threaded locking ring mounted around the nozzle. The locking ring has complete freedom to rotate about the nozzle axis, and limited freedom to translate along the nozzle axis. The length of the shoulder which determines the length by which the nozzle extends outward from locking ring is chosen so that the inventive device is capable of piercing commonly used fluid bag ports when the ring is in a retracted position. In a preferred embodiment, the nozzle and locking ring are designed so that a finger grip (or two or more finger grips) on the ring may be depressed into engagement with the nozzle as the ring is untwisted. By depressing the finger grip (or grips), the untwisting force supplied to the ring is transformed into push-off force to the female connector, to enable a user to disconnect the inventive device easily from a female luer lock.

The length of the male connector of the invention is preferably reduced to the minimum, given the functions of which it is capable, so that the pressure drop across the connector is less than in conventional free ring connectors. Preferably, the inventive device is dimensioned to meet the ANSI/HIMA MD70.1 and ISO standards.

DETAILED DESCRIPTION OF THE PREFERRED EMBODIMENTS

Figure 1:
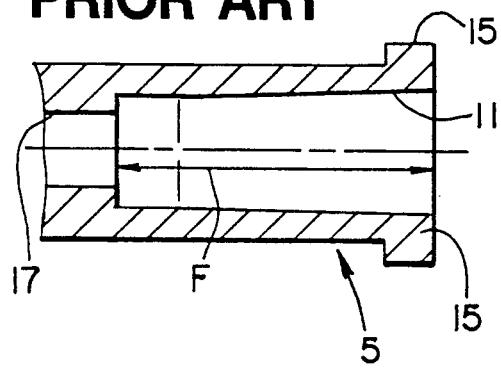
FIG. 1 is a side cross-sectional view of a conventional female luer lock.
Figure 2:
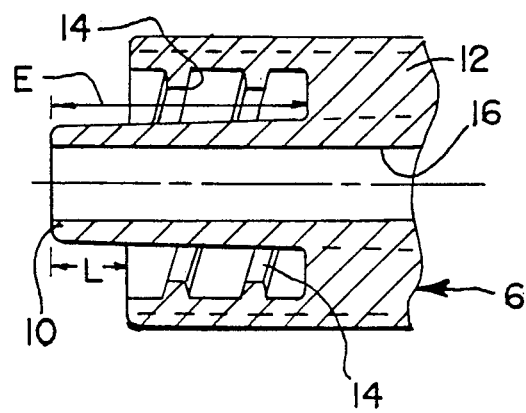
FIG. 2 is a side cross-sectional view of a conventional fixed ring male luer lock.
Figure 2A:
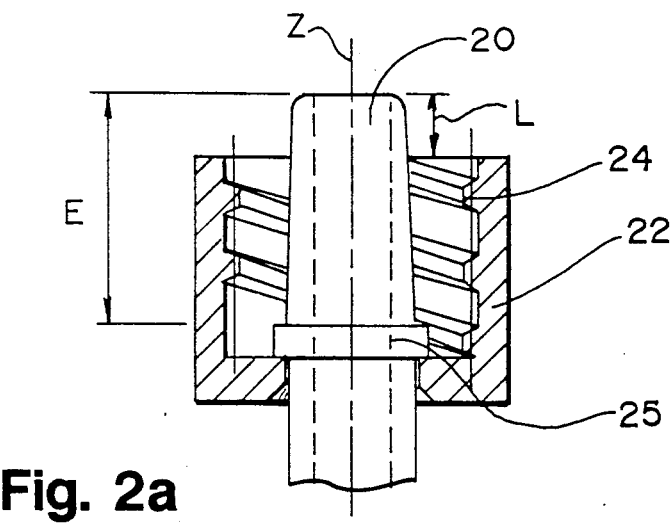
FIG. 2a is a partially side cross-sectional, partially side elevational view of a conventional free ring male luer lock.

A preferred embodiment of the inventive male luer lock will be described with reference to FIGS. 4 through 8. In this embodiment, the invention includes nozzle 300 (shown in FIG. 4) and locking ring 320 (shown in FIG. 5). Ring 320 is designed to be assembled around nozzle 300 with surface 313 of ridge 312 surrounded by ring 320's fingergrip flange 330.

Figure 6:
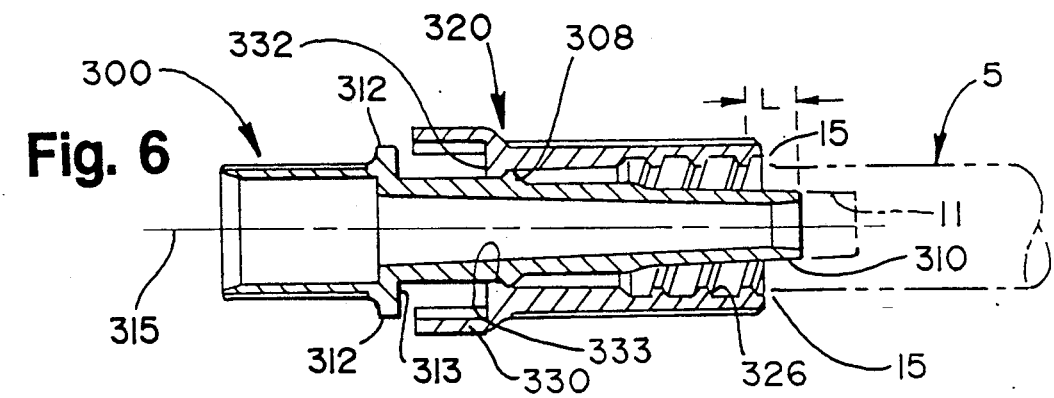
FIGS. 6 and 7 are side cross-sectional views of the FIG. 4 component assembled with the FIG. 5 component, in a retracted and an extended configuration, respectively.

Nozzle 300 has a generally tapered cylindrical shape, and an annular locking ridge 308 protruding radially outward from central longitudinal axis 315. When locking ring 320 is installed around nozzle 300, ridge 308 serves to restrain longitudinal forward motion of ring 320 relative to the nozzle (i.e., motion of ridge 308 away from annular ridge 312 toward nozzle tip 310), so that the extreme "forward" position of ring 320 is as shown in FIG. 6. Annular locking ridge 312 also extends radially outward from axis 315 and serves to restrain longitudinal backward motion of ring 320 by meeting end face 332 of ring 320 (as shown in FIG. 7).

Figure 3:
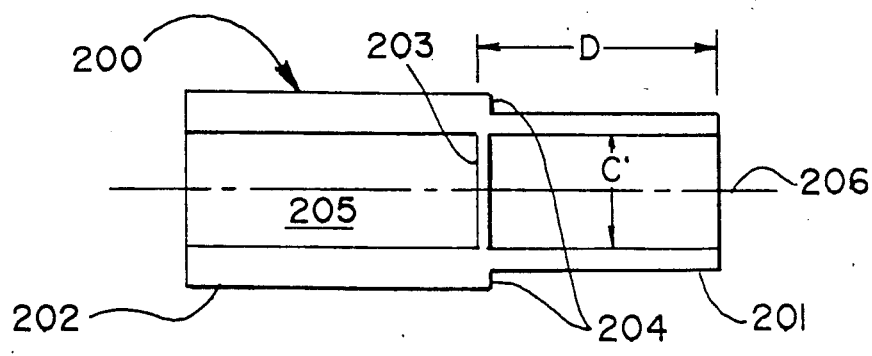
FIG. 3 is a side cross-sectional view of a conventional fluid bag port.
Figure 4:
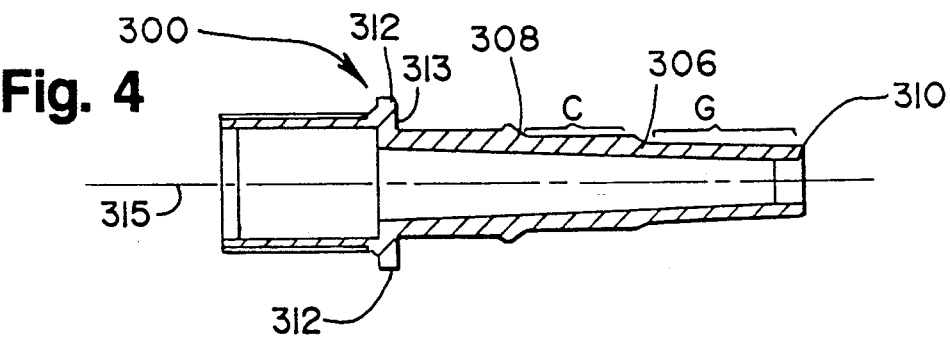
FIG. 4 is a side cross-sectional view of a preferred embodiment of the nozzle portion of the inventive male luer lock.
Figure 5:
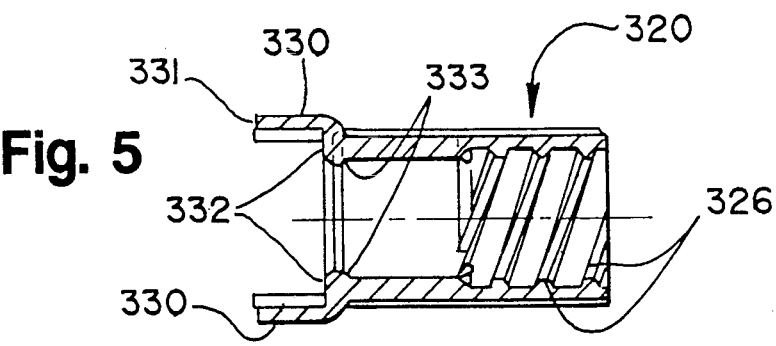
FIG. 5 is a side cross-sectional view of a preferred embodiment of the ring portion of the inventive male luer lock.

Tip 310 of nozzle 300 preferably has a thin profile (i.e., a reduced sidewall thickness) so that nozzle 300 may easily puncture a bag port membrane (such as membrane 203 in FIG. 3). Nozzle 300 has a relatively low diameter end section (with an ANSI/ISO length G) between nozzle tip 310 and shoulder 306, an intermediate diameter section (with an outer diameter C) between shoulder 306 and ridge 308, and a relatively large diameter longitudinal transition section between ridge 308 and locking ridge 312.

Locking ring 320 (shown in FIG. 5) has a generally cylindrical shape, and a cylindrical, flexible, gripping flange 330 which protrudes longitudinally outward at the left end of ring 320. Flange 330 translates untwisting force (applied to ring 320 by a user attempting to disconnect ring 320 and nozzle 300 from a female fitting) into push-off force for pushing the female fitting away from the inventive male fitting. The right portion of ring 320's inner sidewall (in FIGS. 6 and 7) is threaded with helical threads 326 extending radially inward toward the longitudinal axis. An annular locking ridge 333 extends radially inward near opposite end 332 of ring 320 (the non-threaded end of ring 320).

Figure 7:
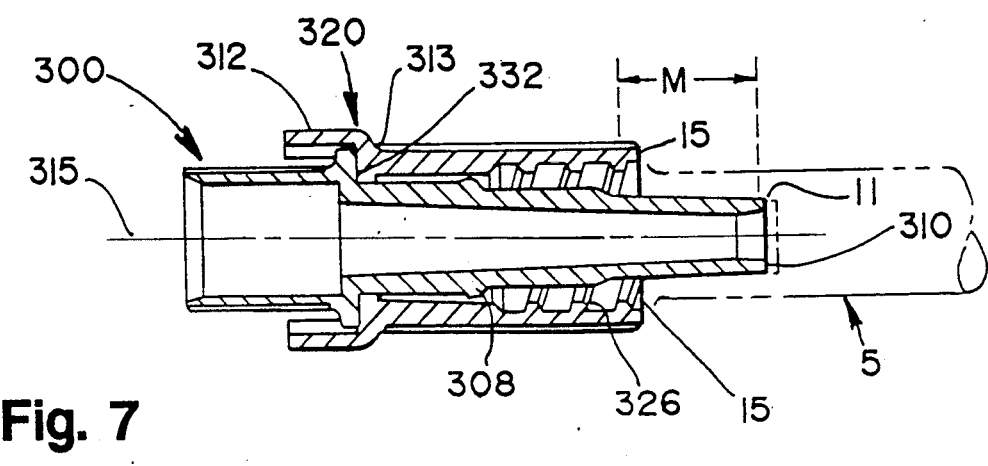

Ring 320 and nozzle 300 are designed to fit together as shown in FIGS. 6 and 7. To install ring 320 around nozzle 300, the non-threaded end of ring 320 is translated toward the left around nozzle 300 (from nozzle tip 310 toward ridge 312) until locking ridge 333 clears ridge 308. The non-threaded end of ring 320 must expand slightly to allow ridge to clear ridge 308. After ridge 333 clears ridge 308, ring 320 has limited freedom to translate longitudinally relative to nozzle 300. In particular, ring 320 is free to translate toward the left until end surface 332 abuts ridge 312 of nozzle 300, (the "bag spiking position" shown in FIG. 7) and ring 320 is free to translate toward the right until ridge 333 abuts ridge 308 (the "fully locked position" shown in FIG. 6).

In the "bag spiking position" shown in FIG. 7, threads 326 of ring 320 have been untwisted as far as possible toward the left (away from female luer lock 5) so that lugs 15 of female luer lock 5 have been expelled from the threads 326. The length M of nozzle 300 which extends toward the right from lugs 15 (i.e., from the right end of ring 320) in the FIG. 7 configuration should be the shortest possible which still allows the tip 310 of nozzle 300 to puncture the membranes of the bag ports with which the device will be used. In the "fully locked position" shown in FIG. 6, a length L (shorter than length M) of nozzle 300 extends toward the right from lugs 15 (i.e., from the right end of ring 320). In a preferred embodiment, the length M is substantially equal to 4.00 mm, and the length L is at least 2.10 mm.

In order to connect the assembled inventive device (shown in FIGS. 6-8) to female luer connector 5 ("luer lock" 5), ring 320 is pushed back to the spiking position shown in FIG. 7 (in which end surface 332 abuts ridge 312), and male nozzle 300 is press fit to the female socket and twisted until lugs 15 of the female connecter engage locking threads 326. Locking ring 320 is then pushed toward the female luer lock and rotated clockwise (bottom to top in FIG. 7) so that threads 326 are screwed onto the female connector (i.e., threads 326 are advanced along lugs 15 of female lock 5), while the outer tapered surface of nozzle 300 slides inside inner tapered surface 11 of luer lock 5. Since locking ring 320 is free to rotate about nozzle 300 (and female luer lock 5), a user may conveniently advance threads 326 along lugs 15 by twisting ring 320 in a first direction (clockwise, if threads 326 are "right-handed") about the common longitudinal axis of nozzle 300 and luer lock 5.

Figure 8:
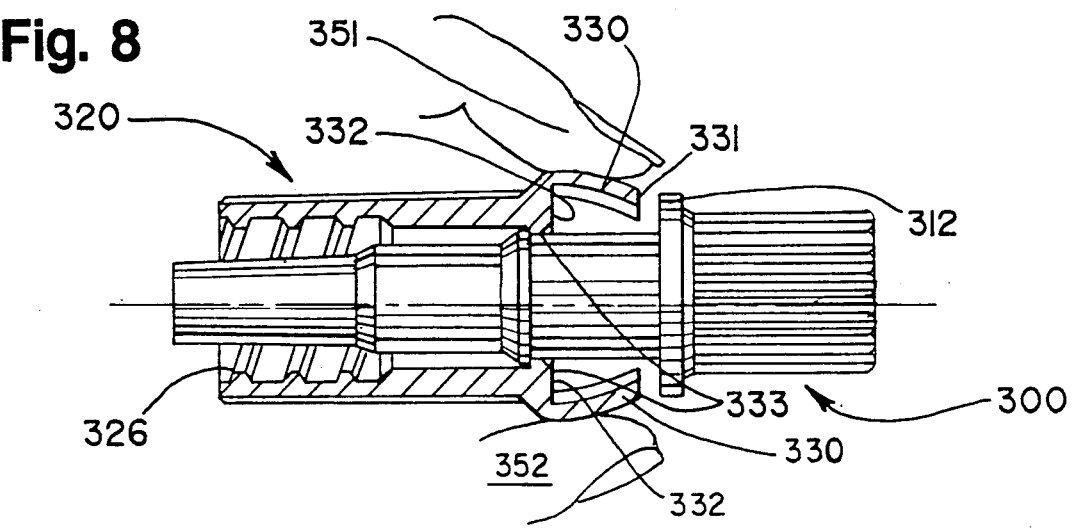
FIG. 8 is a partially side cross-sectional, partially side elevational view of the FIG. 6 assembly with the finger grip in its depressed configuration.
Figure 9:
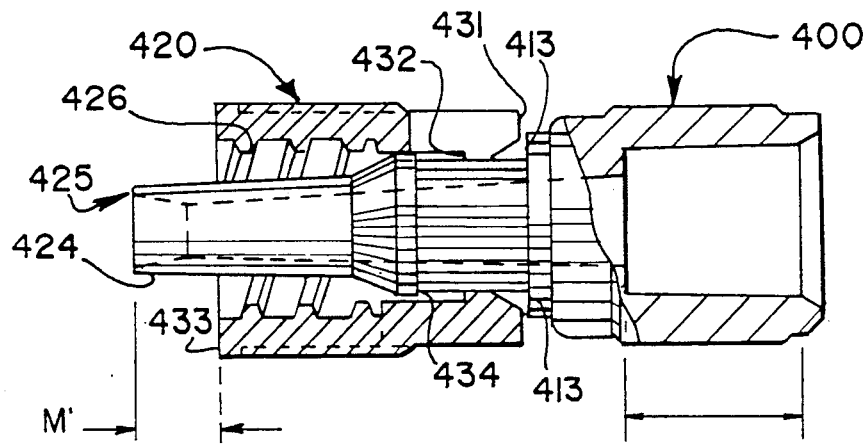
FIG. 9 is a side cross-sectional view of a conventional male luer lock, of the "free/partially restricted" type, with the nozzle in an extended configuration.
Figure 10:
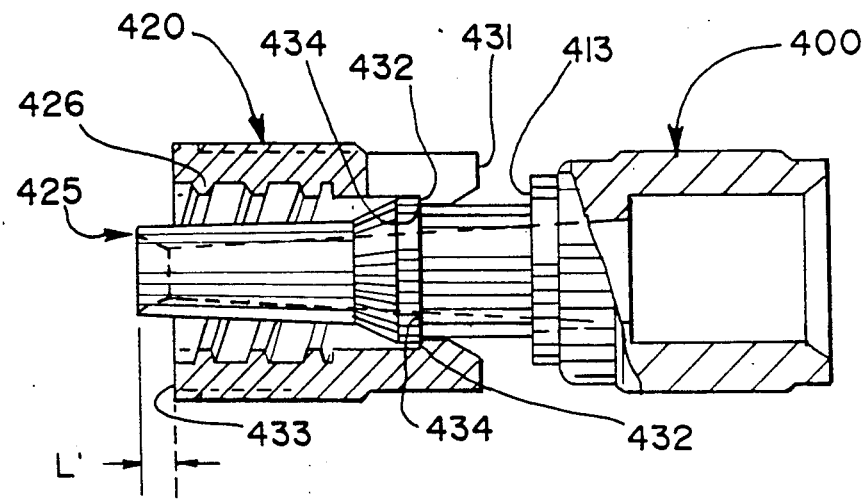
FIG. 10 is a side cross-sectional view of the FIG. 9 assembly, with the nozzle in a retracted configuration.

In order to disconnect the device of FIGS. 6-8 from female luer lock 5, a user will depress flange 330 radially inward, so that its end surface 331 is radially within the outer surface of ridge 312 (as shown in FIG. 8), and then twist ring 320 in the opposite direction (counterclockwise, if threads 326 are "right-handed"). With flange 330 depressed in this manner, the force exerted by ring 320 on nozzle 300 will cause the untwisting force applied to ring 320 to be transformed into a push-off force tending to decouple the female fitting from the inventive male fitting. The unscrewing action of threads 326 will thus advance the female connecter to the left (in FIG. 8) until its frictional bond with male nozzle 300 has been released The length M of nozzle 300's tip portion which extends rightward from the left end of the female luer lock (in the FIG. 7 view, when threads 326 have just decoupled from the female luer lock's lugs) should be the shortest possible which still allows the tip 310 of nozzle 300 to puncture the membranes of the bag ports with which the device will be used. Satisfaction of this criterion will ensure that minimal effort will need to be exerted to overcome friction between nozzle tip 310 and the portion of the female luer lock cavity remaining in engagement with nozzle tip 310 after threads 326 have been withdrawn from the left end of the female luer lock. Thus, a user may exploit the mechanical leverage provided by gripping flange 330 in order to unscrew the female luer lock from threads 326, and the user need not exert substantial "unleveraged" force to separate the male and female luer locks after he or she has unscrewed the female luer lock from threads 326.

In each embodiment of the invention, the inventive device is preferably molded from plastic (for example, polyvinyl chloride). Preferably also, the inventive device meets the ANSI/HIMA MD70.1 and ISO standards, and is designed for use with the FIG. 4 bag port (with distance D between membrane 203 and the right end of end portion 201 substantially equal to 9.0 mm, and inner diameter C' of portion 201 substantially equal to 5.1 mm).

It is contemplated that, in the course of a medical procedure, a user may employ the male luer lock of the invention for two purposes: first to spike a bag port; and then to connect with a female luer lock, to provide a passage for fluid flow from the fluid bag to a medical instrument (such as a catheter).

It is contemplated that some embodiments of the inventive device will not meet the ANSI/MINA MD70.1 and ISO standards. It is also contemplated that some embodiments of the inventive device will be specially designed for spiking bag ports having hollow end portions of other than cylindrical shape (and having a membrane at an end of such hollow end portion). Such embodiments will have tapered nozzles with profiles other than the tapered cylindrical profile shown in FIG. 4. For example, for use with a bag port with a hollow rectangular end portion, the tapered nozzle of the inventive device might have a tapered rectangular profile dimensioned to extend through the port's rectangular end portion for piercing the port's membrane. Of course, such "rectangular" embodiment of the inventive male luer lock would be suitable only for connecting with a specially designed female luer lock having a socket with a mating tapered rectangular shape; not for connecting with a conventional female luer lock having a tapered cylindrical socket.

The foregoing is merely illustrative and explanatory of the invention. Various changes in the component sizes and shapes, and other details of the embodiments described herein may be within the scope of the appended claims.

What is claimed is:

1. A male luer lock, capable of connecting with a female luer lock having a tapered socket and lock lugs, comprising:
    a tapered nozzle proportioned to serve as a male luer;
    a threaded locking ring having a distal end and rotatably carried about said tapered nozzle in substantially coaxial manner, said locking ring being capable of limited, longitudinal movement along said nozzle between first and second positions in which the distal end of said nozzle extends farther beyond the distal end of the locking ring in the second position than in the first position; nozzle carrying a locking ridge extending radially outwardly therefrom; longitudinally-extending, radially depressible flange means carried on said locking ring and positioned to normally radially overlap the locking ridge in the second position; said flange means being depressible when the locking ring is in said first position to engage the locking ridge, the longitudinal extent of the threads of said locking ring being greater than the maximum longitudinal spacing between said radially depressible flange means and said locking ridge in said first position, whereby rotation of said locking ring relative to lock lugs of a female luer lock engaging said locking ring threads can cause retraction of both said locking ring and tapered nozzle away from said lugs.

2. The lock of claim 1 wherein the nozzle has a tip end, wherein the nozzle has a pair of longitudinally spaced nozzle ridges, and wherein the locking ring has a ridge positioned longitudinally between the nozzle ridges, when said ring is installed around said nozzle.

3. A dual purpose male luer lock, capable of sequentially piercing a medical fluid container port and connecting with a female luer lock having a tapered socket and lock lugs, comprising:
    a tapered nozzle proportioned to serve as both a port penetrating member and a male luer, said nozzle defining a locking ridge extending radially outwardly therefrom;
    a threaded locking ring having a distal end and rotatably carried about said tapered nozzle in substantially coaxial manner, said locking ring being capable of limited longitudinal movement along said nozzle between first and second positions in which the distal end of said nozzle extends farther beyond the distal end of the locking ring in the second position than in the first position; and longitudinally-extending, radially depressible flange means carried on said locking ring and positioned to normally radially overlap the locking ridge in the second position, said flange means being depressible when the locking ring is in said first position to engage said locking ridge, the longitudinal extent of the threads of said locking ring being greater than the maximum longitudinal spacing between said radially depressible flange mean in said first position and said locking ridge, whereby rotation of said locking ring relative to lock lugs of a female luer lock engaging said locking ring threads can cause retraction of both said locking ring and tapered nozzle away from said lugs.

4. The lock of claim 3 in which a length L of the nozzle extends beyond the distal end of the said locking ring in the first position, and a length M of the nozzle extends beyond the distal end of the locking ring in the second position, and wherein the length M is sufficiently long to allow the nozzle to pierce a medical fluid container port.

5. The lock of claim 4, wherein the nozzle and the locking ring are dimensioned so that, during a disconnection process in which the male luer lock is disconnected from the female luer lock, a tip portion of the nozzle having said length M remains in contact with the female luer lock socket when the threaded portion of the locking ring has been unscrewed just far enough to disengage from the female luer lock.

6. The lock of claim 5, wherein the length M is substantially equal to 4.00 mm, and the length L is at least 2.10 mm.

7. The lock of claim 4, wherein the lock is a dual purpose lock capable of sequentially piercing said medical fluid container port and connecting with a female luer lock having a tapered socket, and wherein the nozzle and the locking ring have dimensions such that, during a disconnection process in which the male luer lock is disconnected from the female luer lock, said length M of the nozzle remains in contact with the female luer lock socket when the threaded portion of the locking ring has been unscrewed just far enough to disengage from the female luer lock.

8. The lock of claim 3, wherein the nozzle is integrally molded from plastic and the locking ring is integrally molded from plastic.

9. The lock of claim 3, wherein the locking ring has a generally cylindrical shape.

10. A male luer lock, capable of connecting with a female luer lock having a tapered socket and lock lugs, comprising:
a tapered nozzle proportioned to serve as a male luer;
a threaded locking ring having a distal end and rotatably carried about said tapered nozzle in substantially coaxial manner, said locking ring being capable of limited, longitudinal movement along said nozzle between first and second positions in which the distal end of said nozzle extends more distally relative to the distal end of the locking ring in the second position than in the fist position; said nozzle carrying a locking ridge extending radially outwardly therefrom; longitudinally-extending, radially depressible flange means carried on said locking ring and positioned to normally radially overlap the locking ridge in the second position; said flange means being depressible when the locking ring is in said first position to engage the locking ridge, the longitudinal extent of the threads of said locking ring being greater than the maximum longitudinal spacing between said radially depressible flange means and said locking ridge in said first position whereby rotation of said locking ring relative to lock lugs of a female luer lock engaging said locking ring threads can cause retraction of both said locking ring and tapered nozzle away from said lugs.

* * * * *